(12) United States Patent
Baturin et al.

(10) Patent No.: US 9,700,267 B2
(45) Date of Patent: Jul. 11, 2017

(54) METHOD AND APPARATUS FOR FABRICATION AND TUNING OF GRATING-BASED DIFFERENTIAL PHASE CONTRAST IMAGING SYSTEM

(71) Applicant: Carestream Health, Inc., Rochester, NY (US)

(72) Inventors: Pavlo Baturin, Rochester, NY (US); Mark E. Shafer, Fairport, NY (US)

(73) Assignee: Carestream Health, Inc., Rochester, NY (US)

( * ) Notice: Subject to any disclaimer, the term of this patent is extended or adjusted under 35 U.S.C. 154(b) by 343 days.

(21) Appl. No.: 14/621,823

(22) Filed: Feb. 13, 2015

(65) Prior Publication Data

US 2016/0038107 A1 Feb. 11, 2016

Related U.S. Application Data

(60) Provisional application No. 61/939,925, filed on Feb. 14, 2014.

(51) Int. Cl.
*G01N 23/04* (2006.01)
*A61B 6/00* (2006.01)

(52) U.S. Cl.
CPC .......... *A61B 6/4035* (2013.01); *A61B 6/4291* (2013.01); *A61B 6/484* (2013.01); *A61B 6/587* (2013.01)

(58) Field of Classification Search
CPC .... A61B 6/484; A61B 6/4291; G01N 23/083; G01N 23/04; G21K 1/06
See application file for complete search history.

(56) References Cited

U.S. PATENT DOCUMENTS

| | | | |
|---|---|---|---|
| 5,812,629 | A | 9/1998 | Clauser |
| 7,346,204 | B2 | 3/2008 | Ito |
| 7,453,981 | B2 | 11/2008 | Baumann et al. |
| 7,639,786 | B2 | 12/2009 | Baumann et al. |
| 7,646,843 | B2 | 1/2010 | Popescu et al. |
| 7,693,256 | B2 | 4/2010 | Brahme et al. |
| 7,817,777 | B2 | 10/2010 | Baumann et al. |
| 8,515,002 | B2 | 8/2013 | Huang et al. |
| 8,855,395 | B2 | 10/2014 | Baturin et al. |
| 9,001,967 | B2 | 4/2015 | Baturin et al. |
| 9,357,975 | B2 | 6/2016 | Baturin et al. |
| 9,494,534 | B2 | 11/2016 | Baturin et al. |

(Continued)

FOREIGN PATENT DOCUMENTS

| | | |
|---|---|---|
| DE | 102006015356 | 8/2007 |
| EP | 1731099 | 12/2006 |

(Continued)

OTHER PUBLICATIONS

International Search Report, International application No. PCT/US2016/062389, mailing date Feb. 2, 2017, 2 pages.

(Continued)

*Primary Examiner* — Courtney Thomas

(57) ABSTRACT

A method for assembling a phase contrast x-ray imaging system includes fabricating a phase grating and an absorption grating according to a preselected pitch of the gratings. The actual obtained pitches are measured and a source grating is then fabricated according to a desired design point of the imaging system.

15 Claims, 7 Drawing Sheets

(56) References Cited

U.S. PATENT DOCUMENTS

| | | | |
|---|---|---|---|
| 2007/0183560 A1 | 8/2007 | Popescu et al. | |
| 2007/0183582 A1 | 8/2007 | Baumann et al. | |
| 2007/0183583 A1 | 8/2007 | Baumann et al. | |
| 2008/0014643 A1 | 1/2008 | Bjorkholm | |
| 2008/0123805 A1 | 5/2008 | Zellerhoff | |
| 2008/0273653 A1 | 11/2008 | Niwa et al. | |
| 2009/0092227 A1 | 4/2009 | David et al. | |
| 2009/0116720 A1 | 5/2009 | Ritman | |
| 2010/0220832 A1 | 9/2010 | Ning et al. | |
| 2010/0220834 A1 | 9/2010 | Heismann et al. | |
| 2010/0246764 A1 | 9/2010 | Itoh et al. | |
| 2010/0246765 A1 | 9/2010 | Murakoshi et al. | |
| 2010/0272235 A1 | 10/2010 | Takahashi | |
| 2011/0085639 A1 | 4/2011 | Nakamura et al. | |
| 2011/0135057 A1 | 6/2011 | Mori et al. | |
| 2011/0206181 A1 | 8/2011 | Linev | |
| 2012/0020461 A1 | 1/2012 | Roessl et al. | |
| 2012/0045108 A1 | 2/2012 | Shechter | |
| 2012/0057677 A1* | 3/2012 | Vogtmeier | G02B 5/1857 378/85 |
| 2012/0093284 A1 | 4/2012 | Takemoto et al. | |
| 2012/0163554 A1 | 6/2012 | Tada | |
| 2012/0250972 A1 | 10/2012 | Tada et al. | |
| 2013/0010926 A1 | 1/2013 | Tada | |
| 2013/0028378 A1 | 1/2013 | Stutman et al. | |
| 2013/0156284 A1 | 6/2013 | Koehler et al. | |
| 2013/0259194 A1 | 10/2013 | Yip et al. | |
| 2013/0308750 A1 | 11/2013 | Ishii | |
| 2014/0044234 A1 | 2/2014 | Hashimoto et al. | |
| 2014/0177789 A1 | 6/2014 | Baturin et al. | |
| 2014/0185746 A1 | 7/2014 | Baturin et al. | |
| 2014/0185896 A1 | 7/2014 | Baturin et al. | |
| 2014/0226782 A1 | 8/2014 | Stutman et al. | |
| 2014/0226783 A1 | 8/2014 | Ning et al. | |
| 2014/0226785 A1 | 8/2014 | Stutman et al. | |
| 2014/0270060 A1 | 9/2014 | Date et al. | |
| 2014/0270061 A1 | 9/2014 | Yamaguchi | |
| 2014/0341347 A1 | 11/2014 | Radicke | |
| 2014/0355740 A1 | 12/2014 | Koehiler et al. | |
| 2015/0092916 A1 | 4/2015 | Baturin et al. | |
| 2015/0110247 A1 | 4/2015 | Baturin et al. | |
| 2015/0117599 A1 | 4/2015 | Yun et al. | |
| 2015/0187096 A1 | 7/2015 | Baturin et al. | |
| 2015/0216499 A1 | 8/2015 | Martens et al. | |
| 2016/0038107 A1 | 2/2016 | Baturin et al. | |
| 2016/0095562 A1 | 4/2016 | Baturin et al. | |

FOREIGN PATENT DOCUMENTS

| | | |
|---|---|---|
| WO | 2011/122715 | 10/2011 |
| WO | 2012/029048 | 3/2012 |
| WO | 2012/080125 | 6/2012 |
| WO | 2013/126296 | 8/2013 |
| WO | 2014/137318 | 9/2014 |

OTHER PUBLICATIONS

Jian Fu et al., Helical differential X-Ray phase-contrast computed tomography, Physica Medica, vol. 30, pp. 374-379, 2014.

Chapman, D., Thomlinson, et al., "Diffraction enhanced x-ray imaging," Phys. Med. Biol., 42, 2015, (1997).

Bonse, et al., "An x-ray interferometer," Appl. Phys. Lett. 6(8), 155-156, (1965).

Ingal. V. N., et al., "X-ray plane-wave topography observation of the phase contrast from non-crystalline object," J. Phys. D 28(11), 2314-2317, (1995).

Wilkins, S. W., et al., "Phase-contrast imaging using polychromatic hard X-rays," Nature (London) 384(6607) 335-338, (1996).

Momose, A., et al., "Demonstration of X-ray Talbot interferometry," Jpn. J. Appl. Phys. 42, L866-L868, (2003).

Wietkamp, T., et al., "X-ray phase imaging with a grating interferometer," Opt. Exp. 13(16), 6296-6304, (2006).

Pfeiffer, F., et al., "Phase retrieval and differential phase-contrast imaging with low-brilliance X-ray sources," Nature Phys. 2, 258-261 (2006).

International Search Report, International application No. PCT/US2014/066027, mailing date May 2, 2015, 2 pages.

International Search Report, International application No. PCT/US2014/066033, mailing date Apr 28, 2015, 2 pages.

International Search Report, International application No. PCT/US2013/026301, mailing date Jun 3, 2013, 3 pages.

International Search Report, International application No. PCT/US2013/075898, mailing date Apr 22, 2014, 2 pages.

Supplementary European Search Report, dated Nov. 27, 2015, European Application No. 13769560.7, 2 pages.

Thomas Thuring, Compact X-ray grating interferometry for phase and dark-field computed tomography in the diagnostic energy range, Swiss Federal Institute of Technology Zurich, 2013, pp. 1-180.

Thomas Thuring, et al., Non-linear regularized phase retrieval for unidirectional X-ray differential phase contrast radiography, Optics Express, vol. 19, Issue 25, pp. 25545-25558, Optical Society of America 2011, issn: 10944087.

C. Kottler et al., Grating interferometer based scanning setup for hard x-ray phase contrast imaging, Review of Scientific Instruments, vol. 78, 034710, 2007, pp. 1-4.

H.N. Cardinal and A. Fenster "An accurate method for direct dual-energy calibration and decomposition" Medical Physics, May-Jun. 1990; vol. 17, No. 3, pp. 327-341.

* cited by examiner

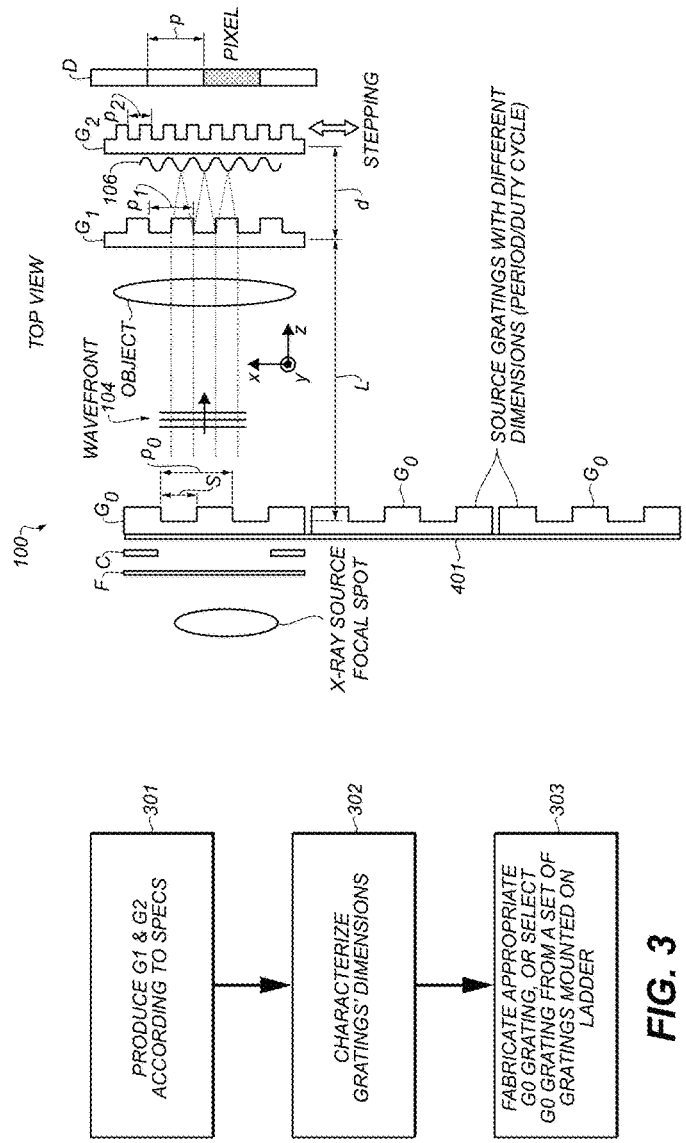

| IMAGE | METHOD | ANGULAR TILT OF MOIRE PATTERN, α (DEGREES) | PERIOD, T' (mm) | FREQUENCY, f' (cyc/mm) | ROTATION ANGLE BETWEEN G1 AND G2 GRATINGS, θ (DEGREES) | ABS (Δθ) (DEGREES) |
|---|---|---|---|---|---|---|
| 1ST, $\theta_0$ | EXPER. | -69.69 | 0.388 | 2.581 | | |
| | THEOR. | | 0.381 | 2.628 | -0.283 | 0.12823 |
| 2ND, $\theta_0 + \Delta\theta$ | EXPER. | -55.78 | 0.633 | 1.58 | | |
| | THEOR. | | 0.610 | 1.64 | -0.155 | 0.13259 |
| 3RD, $\theta_0 + 2\Delta\theta$ | EXPER. | -11.86 | 1.112 | 0.900 | | |
| | THEOR. | | 1.063 | 0.941 | -0.022 | 0.13072 |
| 4TH, $\theta_0 + 3\Delta\theta$ | EXPER. | 45.87 | 0.757 | 1.322 | | |
| | THEOR. | | 0.759 | 1.318 | 0.109 | AVERAGE ABS (Δθ) = 0.131 |

METHOD AND APPARATUS FOR FABRICATION AND TUNING OF GRATING-BASED DIFFERENTIAL PHASE CONTRAST IMAGING SYSTEM

CROSS REFERENCE TO RELATED APPLICATIONS

This application claims priority to U.S. patent application Ser. No. 61/939,925, filed Feb. 14, 2014, in the name of Baturin et al., and entitled "METHOD AND APPARATUS FOR FABRICATION AND TUNING OF GRATING-BASED DIFFERENTIAL PHASE CONTRAST IMAGING SYSTEM."

This application is related in certain respects to U.S. patent application Ser. No. 14/143,254, filed Dec. 30, 2013, in the name of Baturin et al., and entitled LARGE FOV PHASE CONTRAST IMAGING BASED ON DETUNED CONFIGURATION INCLUDING ACQUISITION AND RECONSTRUCTION TECHNIQUES; U.S. patent application Ser. No. 13/729,443, filed Dec. 28, 2012, in the name of Baturin et al., and entitled SPECTRAL GRATING-BASED DIFFERENTIAL PHASE CONTRAST SYSTEM FOR MEDICAL RADIOGRAPHIC IMAGING; and U.S. patent application Ser. No. 13/724,096, filed Dec. 21, 2012, in the name of Baturin et al., and entitled GRATING-BASED DIFFERENTIAL PHASE CONTRAST IMAGING SYSTEM WITH ADJUSTABLE CAPTURE TECHNIQUE FOR MEDICAL RADIOGRAPHIC IMAGING, all of which are hereby incorporated by reference as if fully set forth herein in their entirety.

BACKGROUND OF THE INVENTION

The subject matter disclosed herein relates to differential phase contrast imaging (DPCI), in particular, to methods and apparatus for optimizing grating alignment and grating dimensions to produce maximum phase contrast.

Phase contrast imaging (PCI) has emerged over the last several years as a useful imaging technique capable of probing phase characteristics of an object as complimentary information to its conventional absorption properties. Although, to date, several PCI techniques have been explored, some effort has been made to develop a grating-based DPCI technique that enables the use of a conventional broadband X-ray source. Conventional medical X-ray imaging devices rely on material absorption properties to provide information about an object's interior structure. While good contrast between strongly (hard) and weakly (soft) attenuating materials can be achieved, soft tissue differentiation can be difficult due to low relative contrast. For example, the low-contrast soft tissue materials including, but not limited to, vessels, cartilage, lung, and breast tissue, provide poor contrast in comparison to highly attenuating bone structures. The problem with soft-tissue imaging may be addressed by interferometric X-ray imaging devices, which utilize the wave nature of X-ray radiation. In addition to conventional absorption, such devices measure the phase shift experienced by an X-ray beam traversing the imaged object. The significantly larger atomic cross section of phase shift in comparison to absorption creates the potential for better sensitivity to material differentiation.

Several PCI imaging techniques may prove useful, including an interferometer technique, a diffraction-enhanced imaging technique, and a free-space propagation technique. Various difficulties associated with these techniques, such as the requirement of a synchrotron or micro-focus X-ray source, high sensitivity to mechanical instability, and large propagation distances, impose practical limitations on the development of clinically useful systems. Grating-based systems, such as Talbot-Lau PCI, may make possible an interferometer-based PCI system using a broadband X-ray source. Such a system takes advantage of the Talbot self-imaging interferometric effect to detect local phase shifts in the imaged object. Also, the geometrical alignment of the gratings may provide another technique for PCI system optimization.

An exemplary DPCI system may be assembled as shown in FIG. 1. The DPCI system 100 may include a polychromatic X-ray source 102 aimed at a beam shaping assembly that includes a filter F and a collimator C. Other assembled components of the DPCI system 100 placed in the path of the shaped x-ray beam include a partially absorbing source grating $G_0$, an interferometric phase grating $G_1$, a partially absorbing grating $G_2$ (absorption grating), and an X-ray detector D which captures a radiographic image of an object 105. As illustrated, the object 105 is disposed between the source grating $G_0$ and the phase grating $G_1$. The openings s in source grating $G_0$ each may have a period $p_0$ of about tens of micrometers, which create partially coherent X-ray radiation 104 entering phase grating $G_1$. Phase grating $G_1$ may have a period $p_1$ of about a few micrometers, which is less than $p_0$, and generates a self-imaging interference pattern 106 which is further modulated by absorption grating $G_2$, having a period $p_2$ smaller than $p_1$, onto an X-ray detector D. The gratings themselves may be made using well known manufacturing methods. The dimensions of the gratings, such as the periods ($p_0$, $p_1$, $p_2$), or pitch, are fairly well controllable and may be manufactured according to desired design points. The imaging performance of such a system depends on grating dimensions, the geometry of the PCI setup (i.e., the relative position of the X-ray source, gratings (e.g., distances L and d), object, and X-ray receptor), X-ray beam quality, and detector properties.

The discussion above is merely provided for general background information and is not intended to be used as an aid in determining the scope of the claimed subject matter.

BRIEF DESCRIPTION OF THE INVENTION

A Moiré fringe pattern frequency and angular orientation produced in the plane of the X-ray detector D of the DPCI system 100 is a function of the gratings' axial rotation about the axis z. Axial displacement (along the z axis) as between source-to-phase (L) and phase-to-absorption (d) gratings affects system contrast. The L–d regions of highest contrast may be implemented according to design considerations, as described herein, including effects of the X-ray spectrum on image contrast. As will be described herein below, performance of the PCI system is also highly sensitive to alignment of the gratings.

A DPCI system's geometrical dimensions may be used to estimate how the system's alignment affects a frequency of a Moiré fringe pattern and system imaging contrast. Scans and analysis may be conducted by the DPCI system 100 to identify the L–d dimensions that provide optimal contrast in captured radiographic images. The optimization process of such a DPCI system can be explained with respect to both (i) relative alignment of the gratings, and (ii) identification of the L–d magnitudes.

In one embodiment, a grating-based differential phase contrast imaging (DPCI) system provides a controllable Moiré frequency pattern. The frequency may be primarily controlled by changing dimensions of a source grating $G_0$, for example, attaching $G_0$s with different dimensions to a ladder 401, or gratings holder, and having them swapped by moving the ladder perpendicular to a direction of the X-ray beam 104 (FIG. 4) in a DPCI system 100. The Moiré frequency may be changed by selecting different dimensions (periods) of $G_1$ and $G_2$, however the precision of such a change has about 40-50 times higher sensitivity than for $G_0$. For example, when the periods of gratings G0, G1, and G2 are about 73 µm, 4 µm, and 2 µm, respectively, the frequency of the moiré pattern, which is modulated in the plane of detector D, is around 0.87 cyc/mm. In order to tune DPCI system to zero moiré frequency it may be sufficient to change dimensions of $G_0$ by about 7% (to approximately 78 µm), while the dimensions of $G_1$ or $G_2$ would have to be changed by about 0.17%. When the periods of $G_1$ and $G_2$ are in the order of just few micrometers the 0.17% change in dimension may be difficult to realize. In one embodiment, the period of $G_0$ grating may be about 73 µm, and a 7% change equates to about a 5 µm change, which may be easier to manufacture with high precision. Therefore, it would be desirable to fabricate $G_1$ and $G_2$, characterize (measure) them and, based on such measurements, provide an appropriately dimensioned $G_0$, which could be designed to yield a "tuned" or a "detuned" configuration, as desired. The control of the Moiré frequency would be important for both a tuned PCI configuration ($\Delta f=0$) and detuned ($\Delta f \neq 0$). Here, $\Delta f$ refers to a frequency of Moire pattern modulated in the plane of detector D, and may be referenced herein as f'. For a tuned configuration, one needs to be able to adjust (or optimize) the system by selecting $G_0$s in order to obtain a minimal or zero Moiré frequency. For detuned configurations the frequency is an important factor which determines the number and size of the steps (or shifts) of the object (or interferometer arm), and the control of frequency is necessary if any alteration in stepping is desired. If the ratio of optimal L-d positions is denoted as $\eta=L/d$, then the sensitivities (or relative changes) necessary for changing the frequency of moiré pattern from $\Delta f=0.87$ cyc/mm to ~0 cyc/mm would be $$\delta p_0 = \frac{2p_2\eta - p_1\eta - p_1}{(2p_2 - p_1)\eta}, \quad \delta p_2 = \frac{2p_0\eta^{-1} - p_1\eta^{-1} - p_1}{(2p_0 - p_1)\eta^{-1}}$$

for G0 and G2 gratings, respectively. Here $p_1$, $p_2$, and $p_0$ are the periods of G0, G1, and G2.

In another embodiment, a DPCI system includes swappable (or movable) $G_0$ gratings to control Moiré frequency. A phase grating and an absorption grating are manufactured according to a desired pitch of the gratings and installed in a phase contrast imaging system. An actual pitch of the gratings are determined, followed by selecting a source grating from a plurality of source gratings secured in a gratings holder of the imaging system, and using the selected source grating for radiographic imaging by the system.

In another embodiment, an assembly method includes a defined order of system fabrication, where $G_1$ and $G_2$ are fabricated first, $G_0$ desired dimensions are then determined and designed according to actual (i.e., measured) dimensions of $G_1$ and $G_2$. Thus, fabrication of a phase grating and an absorption grating are performed first according to a selected pitch of the gratings. The actual pitch of the fabricated phase grating and absorption grating is determined, and a desired source grating is fabricated based on the determined pitch of the phase and absorption gratings.

The summary descriptions above are not meant to describe individual separate embodiments whose elements are not interchangeable. In fact, many of the elements described as related to a particular embodiment can be used together with, and possibly interchanged with, elements of other described embodiments. Many changes and modifications may be made within the scope of the present invention without departing from the spirit thereof, and the invention includes all such modifications. The drawings below are intended to be drawn neither to any precise scale with respect to relative size, angular relationship, relative position, or timing relationship, nor to any combinational relationship with respect to interchangeability, substitution, or representation of a required implementation.

This brief description of the invention is intended only to provide a brief overview of subject matter disclosed herein according to one or more illustrative embodiments, and does not serve as a guide to interpreting the claims or to define or limit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. The drawings are not necessarily to scale, emphasis generally being placed upon illustrating the features of certain embodiments of the invention. In the drawings, like numerals are used to indicate like parts throughout the various views. Thus, for further understanding of the invention, reference can be made to the following detailed description, read in connection with the drawings in which:

FIG. 3 is a flow diagram of an exemplary gratings fabrication method;

FIG. 4 is a schematic diagram of a top view of another exemplary three-grating DPCI system with fixed gratings $G_1$ and $G_2$ and variable grating $G_0$ mounted on a movable ladder;

DETAILED DESCRIPTION OF THE INVENTION

Figure 1:
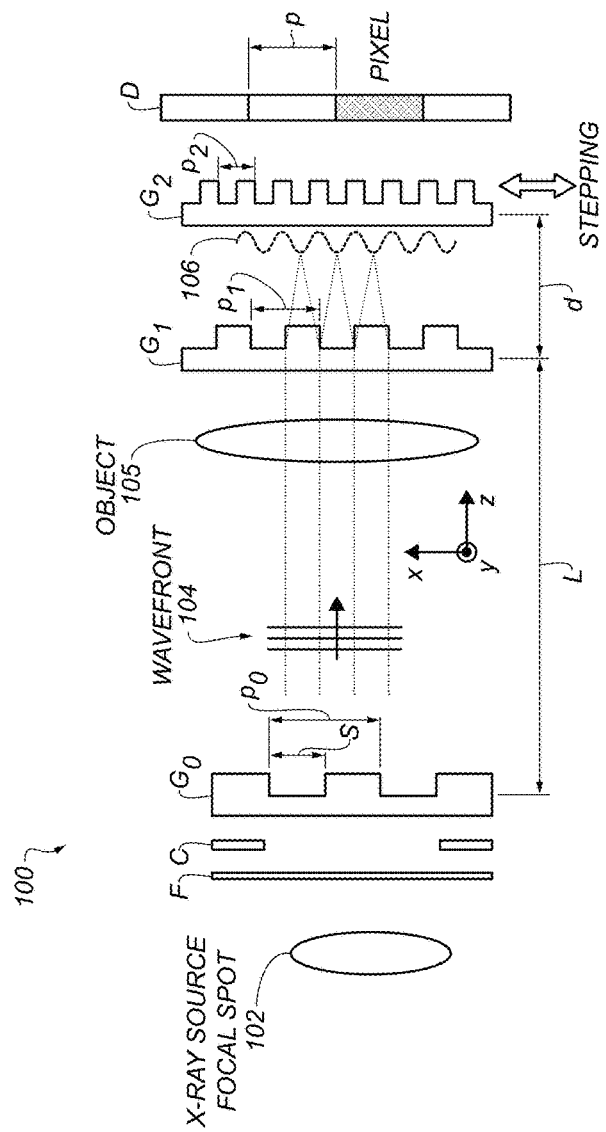
FIG. 1 is a schematic diagram of a top view of an exemplary three-grating DPCI system.

With reference to FIG. 1, the source grating $G_0$ provides an array of individually coherent slit sources, which constructively contribute to image formation when the condition $p_0/L=p_2/d$ is satisfied. In one embodiment, distance L is selected to be about 1.5 m and distance d about 42 mm. The source grating $G_0$ and absorption grating $G_2$ pitches, $p_0$ and $p_2$, respectively, are about 75 µm and 2 µm, respectively. Given that $p_0 \gg p_2$, and the distance L is more than 30 times larger than d, the system 100 performance is not sensitive to precise positioning of $G_0$, and therefore, a rough alignment of grating bars is suitable for use along vertical axis y. In contrast, the relative alignment of $G_1$ and $G_2$ can have a significant impact on the performance of the PCI system. The gratings $G_0$, $G_1$, $G_2$, are disposed in planes substantially parallel to each other and, as described herein, may be purposely rotated, or tilted, about the z axis while remaining parallel.

Figure 2A:
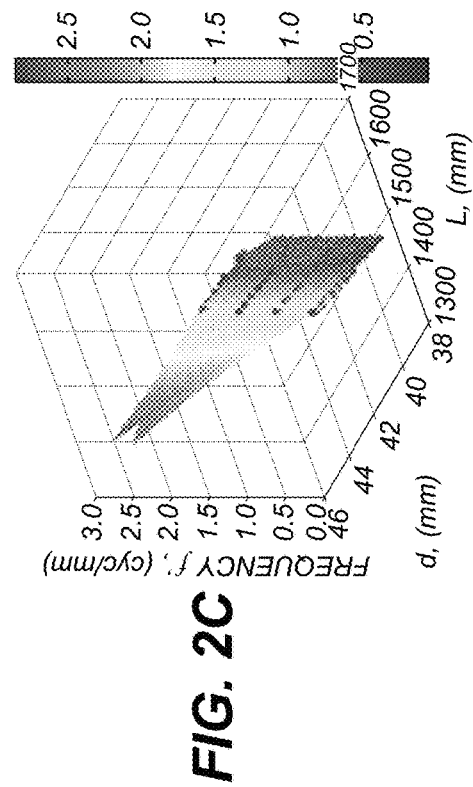
FIGS. 2A-D are contrast and Moiré pattern frequency scans at exemplary 40 kVp and 42 kVp X-ray spectra.
Figure 2C:
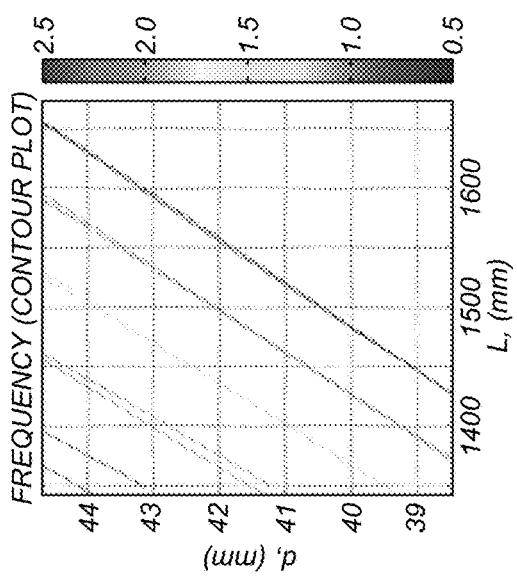
Figure 2B:
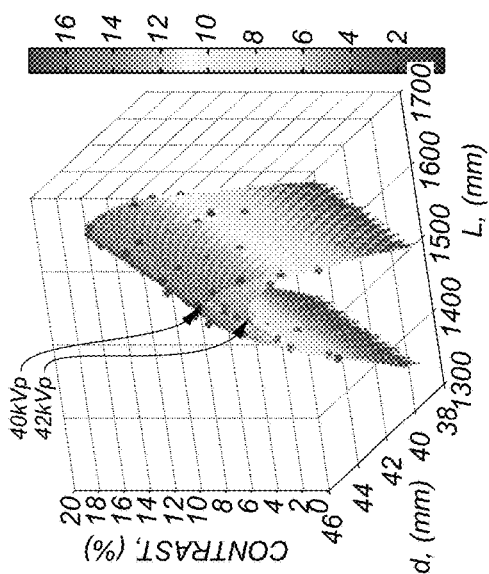
Figure 2D:
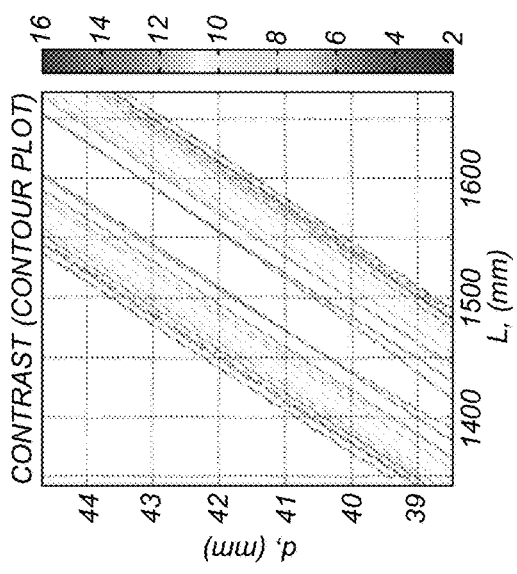

The geometrical properties of a PCI system 100 may be designed to achieve maximum imaging contrast. In one embodiment, the distance L from source grating $G_0$ to phase grating $G_1$ and distance d between phase $G_1$ and absorption $G_2$ grating may be selected for optimal system contrast. FIGS. 2A-D illustrates a range of values for L and d and their resultant system performance in terms of contrast (FIGS. 2A-B) and frequency (FIGS. 2C-D). In addition, the gratings' dimensions and angular alignment are factors contributing to contrast. Both gratings' dimensions and alignment can change the frequency of the Moiré pattern modulated in the plane of the X-ray detector D. This frequency is a key factor for determining the response of the X-ray detector, i.e., in terms of its modulation transfer function (MTF). In one embodiment, data acquisition in the grating-based PCI system 100 may be performed using phase stepping, and object or interferometer arm stepping.

In one embodiment, the Moiré frequency may be desired to be zero or at least minimized (e.g., a tuned configuration), while in another embodiment the frequency is purposely set to be non-zero (e.g., a detuned configuration). In one embodiment, the maximum contrast of the system is observed at Moiré frequency of about 0.87 cyc/mm. When the L or d distances are altered from their optimal values in order to change the Moiré frequency (i.e., increase or decrease), the contrast of the system drops as shown in FIGS. 2A-D. The data of FIGS. 2A-D were obtained for fixed grating dimensions.

In order to modify or adjust the frequency of the Moiré pattern, it is possible to keep L and d distances at their optimal positions (i.e., in the optimal L–d region) while only changing the gratings' dimensions (i.e., $p_0$, $p_1$ or $p_2$). An analysis of the effects of changing the gratings' dimensions on frequency of the Moiré pattern shows that the $G_1$ or $G_2$ grating dimension change has about a 40-50 times higher sensitivity than for $G_0$. For example, when the periods of gratings G0, G1, and G2 are about 73 µm, 4 µm, and 2 µm, respectively, the frequency of the moiré pattern, which is modulated in the plane of detector D, is around 0.87 cyc/mm. In order to tune DPCI system to zero moiré frequency it may be sufficient to change dimensions of $G_0$ by about 7% (to approximately 78 µm), while the dimensions of $G_1$ or $G_2$ would have to be changed by about 0.17%. When the periods of $G_1$ and $G_2$ are in the order of just few micrometers the 0.17% change in dimension may be difficult to realize. In another embodiment, the period of the $G_0$ grating may be about 73 µm, and a 7% change corresponds to 5 µm, which may be relatively easier to manufacture with high precision.

Therefore, it may be useful to follow the method shown in the flow chart of FIG. 3 to design and build an optimal PCI system. That is, as one step 301 the gratings $G_1$ and $G_2$ are fabricated, using a method directed to obtaining gratings having preselected desired dimensions. The actual dimension obtained after fabrication are verifiably measured and characterized in another step 302. Based on the dimensions of $G_1$ and $G_2$ as fabricated and measured, an appropriate $G_0$ is fabricated or, alternatively, selected from a set of gratings mounted on a ladder, shown in FIG. 4, that permits swapping in and out any one of a plurality of $G_0$ gratings having different periods. The dimensions of the $G_0$ grating may be intended to obtain optimal image contrast when assembled in a DPCI system 100 to capture radiographic images of an object 105.

In demonstrating the feasibility of the methods described herein, we can assume a coordinate system with the y-axis aligned with the direction of the grating bars in $G_2$ (e.g., FIG. 4). The interference pattern 106 generated by the phase grating $G_1$ is a periodic function that repeats the structure of $G_1$ with approximately a two-times-higher frequency according to the Talbot self-imaging effect. The structure of the absorption grating $G_2$ is periodic, as well, because it is designed to repeat the spatial distribution of the interference. Considering only the interference pattern and absorption-grating fundamental frequencies, the modulated signal measured by the detector can be written as:

$$I_D = MTF(f') \otimes I_0 \cdot \Gamma_{1,2} \cdot (\cos(2\pi f_x x + 2\pi f_y y) \cdot \cos(2\pi g_x x + 2\pi g_y y)) = \quad (1)$$

$$MTF(f') \otimes I_0 \cdot \Gamma_{1,2} \cdot \frac{(\cos(2\pi(f_x - g_x)x + 2\pi(f_y - g_y)y) + \cos(2\pi(f_y + g_y)y))}{2}$$

Here, $f_x = \cos(\theta)/d$ and $f_y = \sin(\theta)/d$ are the interference pattern frequencies in the x and y direction, respectively, and $g_{x,y}$ are the frequencies of $G_2$. The relative tilt angle as between gratings $G_1$ and $G_2$ is represented by θ. The X-ray detector MTF is evaluated at a measured frequency $f' = 1/(T'_y \sin(a \tan(T'_x/T'_y)))$ with periods $T'_x = 1/(f_x - g_x)$ and $T'_y = 1/(f_y - g_y)$. Here, $I_0$ is the intensity of the X-ray beam incident on $G_1$ grating, and $\Gamma_2$ is the average transmission through $G_1$ and $G_2$. Due to the micrometer dimensions of $G_1$ grating, the frequencies $f_x$ and $g_x$ are in the order of 500 cyc/mm and cannot be detected. Therefore, the frequency summation term in the x direction has been omitted from Eq. (1). The Moiré pattern modulated by $G_2$ onto the detector would have frequency f' and angle α relative to the vertical y-axis, where $$\alpha = \tan^{-1}((f_y - g_y)/(f_x - g_x)) \quad (2)$$

Figure 5C:
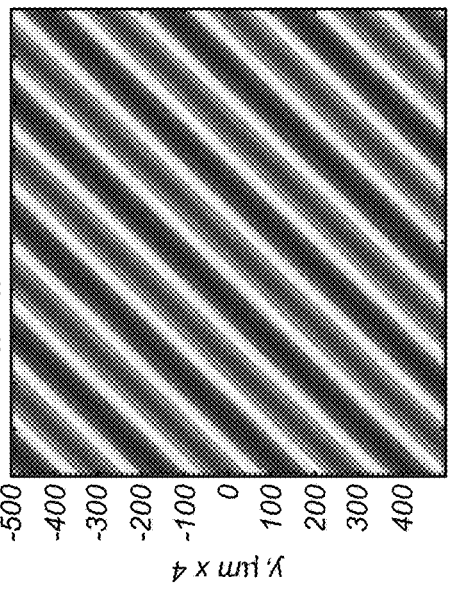
FIGS. 5A-D are diagrams of exemplary Moiré patterns in the plane of the detector for tilt angles θ of about 0.1° and about 0.2°, and for ($f_x-g_x$) magnitudes equal to about 0 cyc/mm and about 1 cyc/mm.
Figure 5D:
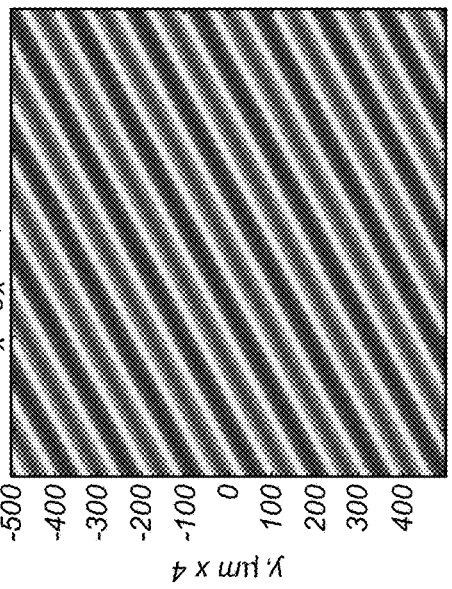
Figure 5A:
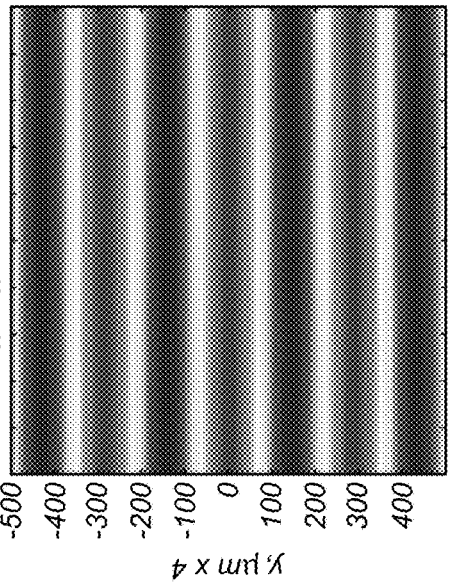
Figure 5B:
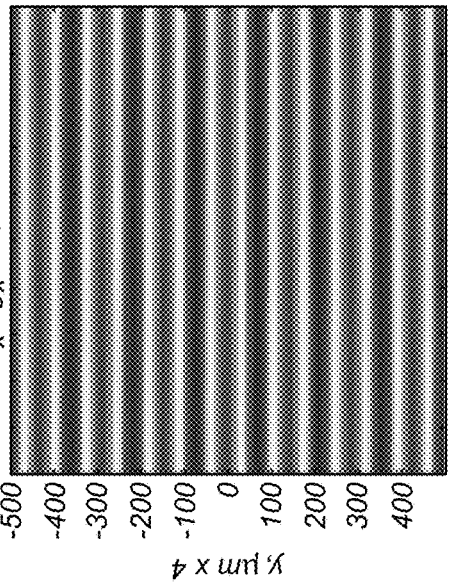

To achieve the maximum PCI system performance, the periods of $G_1$ and $G_2$ are manufactured such that the interference pattern period produced by $G_1$ at Talbot distance d matches the period of $G_2$ (i.e., $f_x = g_x$). In such a case, perfectly aligned gratings (θ=0°) would yield a uniform image for an open-field exposure. Tilting of one of the gratings using z as the rotational (tilt) axis at an angle θ (θ≠0°) would result in horizontally oriented Moiré fringes. In practice, frequencies $f_x$ and $g_x$ might not be exactly equal ($f_x \neq g_x$). In such a case, the Moiré pattern with frequency f' and angle α between fringes and vertical axis y is expected. The Moiré patterns produced at two different tilt angles θ=0.1° and θ=0.2° are shown in FIGS. 5A-D for $f_x=g_x$ (FIGS. 5A-B) and for $f_x-g_x=1$ cyc/mm cases (FIGS. 5C-D). The geometrical rationale extracted from Eq. (1) was used to generate images in FIGS. 5A-D. The images confirm that the frequency of Moiré fringes increases for larger θ. In addition, the tilt of the fringes by angle α in $f_x-g_x=1$ cyc/mm case is larger when the stronger misalignment between $G_1$ and $G_2$ (i.e., larger θ) is observed.

Figure 6:
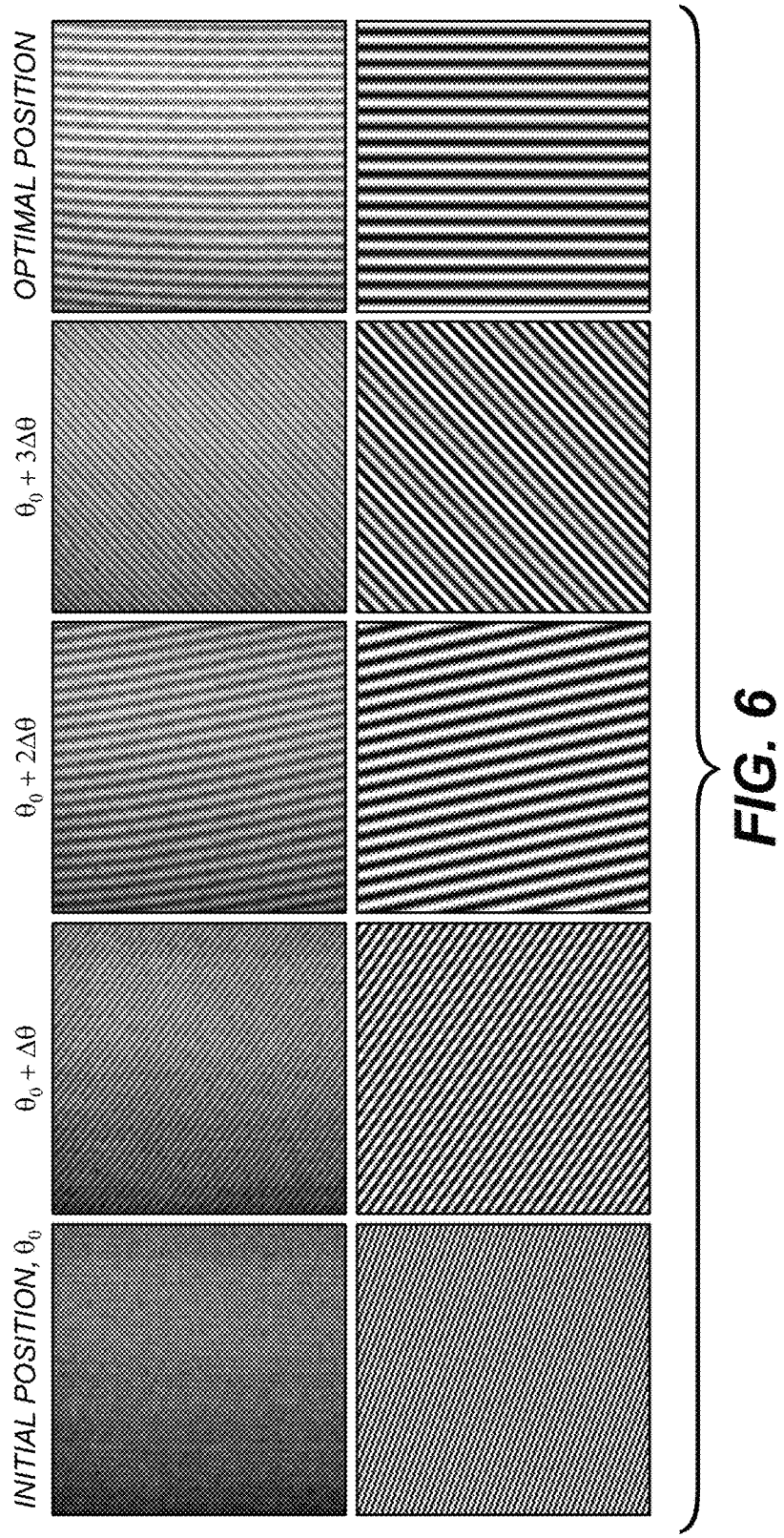
FIG. 6 are experimental measurements (top row) and simulations (bottom row) of Moiré patterns as a function of the angular rotation of the $G_1$ grating relative to $G_2$.

The effects illustrated in FIGS. 5A-D were confirmed using a three-grating Talbot-Lau interferometer experimental setup similar to the system shown in FIG. 1. The $G_1$ grating was axially rotated (i.e., in the XY plane) four times using angular steps (Δθ) of about 0.133°, and the Moiré pattern's angle α and frequency f' were determined from the image data. FIG. 6 shows the open-field images experimentally measured (top row) and simulated using the geometrical rationale of Eq. (1) (bottom row). The first four images in both rows (from left to right) correspond to a different rotation angle θ, while the images in the fifth position of each row represent an optimal setting. The frequency of the Moiré pattern observed in the images changes depending on the relative rotational angle of the gratings. In addition, the contrast of the images is a function of the frequency of the Moiré fringes. Namely, the contrast, which is low at high Moiré frequency, increases when the frequency approaches the optimal conditions (i.e., perfectly aligned gratings). Note that simulated images do not include the MTF of the detector and, therefore, only exhibit rotational tilt and frequency of the expected Moiré pattern. As the Moiré patterns of FIG. 5 illustrate, the frequency and tilt of the fringes are consistent between the experiment and the modeling. The Moiré pattern's angle α and frequency f' determined from the experimental images are presented in the table of FIG. 7 in the rows marked "exper." Furthermore, these measurements were used to theoretically predict the frequency of the Moiré fringes and the angle of the gratings' rotation θ, according to the geometrical properties described herein. The mean value of the estimated grating rotation Δθ between X-ray exposures (images) was found to be 0.131°, consistent with the 0.133° incremental rotation achieved by mechanical adjustment.

In addition to the relative gratings' axial rotation, the axial distances L and d are important for optimization of the imaging system's contrast. To find the L-d regions of optimal contrast, a series of polychromatic X-ray exposures was conducted at different L and d distances. With each run, the contrast and frequency were measured. Next, both data sets were fit with a second-order polynomial, and the results are shown in FIGS. 2A-D.

Geometrical alignment of the system should follow the equations:

$$d_{pl} = \frac{np_1^2}{8\lambda}, \quad (4)$$

$$d_{sp} = \frac{Ld_{pl}}{L - d_{pl}}, \quad (5)$$

$$\frac{p_0}{L} = \frac{p_2}{d_{sp}}, \quad (6)$$

$$p_{int} = \frac{p_1}{2} \frac{d_{sp} + L}{L}, \text{ and} \quad (7)$$

$$f' = \frac{1}{p_{int}} - \frac{1}{p_2}. \quad (8)$$

Equation (4) specifies the position of the Talbot self-imaging (n is a Talbot order) for plane waves with wavelength λ. When diverging spherical waves are used, the optimal self-imaging position changes to $d_{sp}$. Equation (6) is an alignment requirement for forming constructive interference with the period defined by Equation (7). The frequency of the modulated Moiré pattern can be calculated by Equation (8). Using Eqs. (7) and (8), it can be shown that the Moiré frequency can be written as:

$$f'=(2p_2\chi-p_1)/(p_1p_2), \quad (9)$$

where $\chi=L/(L+d_{sp})$. When the imaging system is designed, the period of $G_2$ may be chosen to be equal to $p_{int}$, so we can write: $p^*_2=p_1/(2\chi^*)$, whereby at (*) we denote the designed value. Substituting $p_2^*$ into Equation (9), we can obtain the frequency:

$$f'=L/(L^*p_2)((d_{sp}^*+L^*)/(d_{sp}+L)-1).$$

Figure 9B:
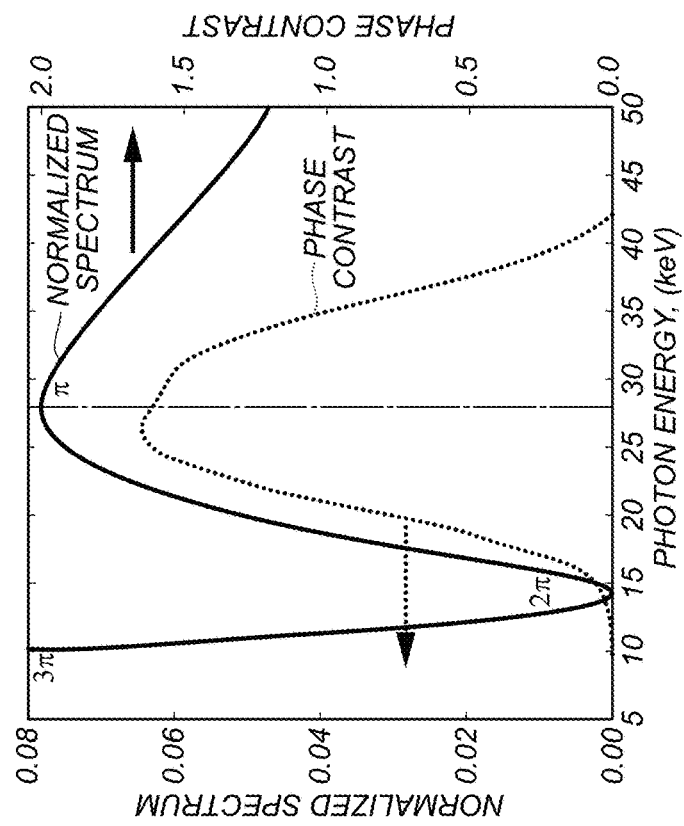
FIGS. 9A-B are plots of the 40 kVp (FIGS. 2A-D) normalized X-ray spectrum superimposed with the phase shift caused by the 36 µm Si structure of the $G_1$ grating (9A), and phase contrast formed by the phase shift (9B).

If L is fixed at desired distance L*, then the Moiré frequency is:

$$|f'|\propto \Delta d_{sp}/(p_2L), \quad (10)$$

where $\Delta dsp$ is a displacement in distance between $G_1$ and $G_2$ (i.e., $d_{sp}=d_{sp}^*\pm\Delta d_{sp}$). Thus, the frequency of the Moiré pattern is expected to change linearly with the change of d at fixed L. This is shown in the frequency plot of FIG. 9 although, it should be noted, due to a mismatch in the gratings' dimensions, the frequency of the Moiré pattern happens to be about 0.8 cyc/mm. As the frequency increases, the detector's MTF reduces the contrast of the system, as seen in the contrast plot (FIG. 9B). The linear trend of the optimal L-d region follows a linear dependence in Eq. (6), i.e., $L=p_0/p_2d_{sp}$. Using Eqs. (5)-(7), it can be shown that the period of the interference pattern can be written as: $p_{int}=p_1(p_0+p_2)/(2p_0)$. For a case of tuned system $p_{int}=p_2$, we get: $p_0=p_1\cdot p_2/(2\cdot p_2-p_1)$. When it is used in Eq. (8), the frequency of the Moiré pattern would only depend on grating periods $p_0$, $p_1$, and $p_2$, and it is independent of the energy of the X-ray spectrum. This is observed in FIGS. 2A-D, where the frequency stays the same for 40 and 42 kVp spectra, and the L-d regions are identical. It may be noted that the contrast of the system in the optimal L-d region is smaller for the 42 kVp spectrum, because the mean energy of the 42 kVp spectrum is no longer optimal for phase grating $G_1$ (in our case, designed for the 40 kVp spectrum).

Figures 7, 8:
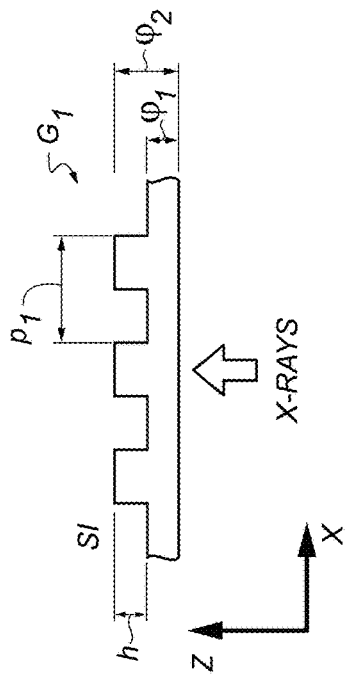
FIG. 7 is a table of measured and theoretically derived Moiré pattern data based on the images presented in FIG. 6.
FIG. 8 is a schematic of phase grating $G_1$.

The drop in contrast for the higher energy of the X-ray spectrum may be explained by examining phase grating $G_1$, as shown in FIG. 8. When the X-ray beam passes through the grating, it experiences the phase shift φ, which is a function of the material (as defined by the decrement of the index of refraction δ) and its thickness Δz:

$$\varphi(x, y) = -\frac{2\pi}{\lambda}\delta\Delta z \quad (11)$$

This phase shift is a part of the transmission function T(x,y):

$$T(x,y)=e^{i\phi}A(x,y) \quad (12)$$

where A(x,y) is the amplitude of the absorption. The groove structure of the grating will yield different phase shifts, as shown in FIG. 8. The contrast of the system will be proportional to the amplitude of the phase modulation:

$$amp = |e^{i\phi_2} - e^{i\phi_1}| \quad (13)$$

The maximum phase amplitude would occur when the phase difference of π between $\phi_1$ and $\phi_2$ is achieved. For example, if $\phi_1=0$ and $\phi_2=\pi$, then amp=2. This sets the optimal height of the phase grating structure to be:

$$h_1 = \frac{\lambda}{2\delta} \quad (14)$$

Figure 9A:
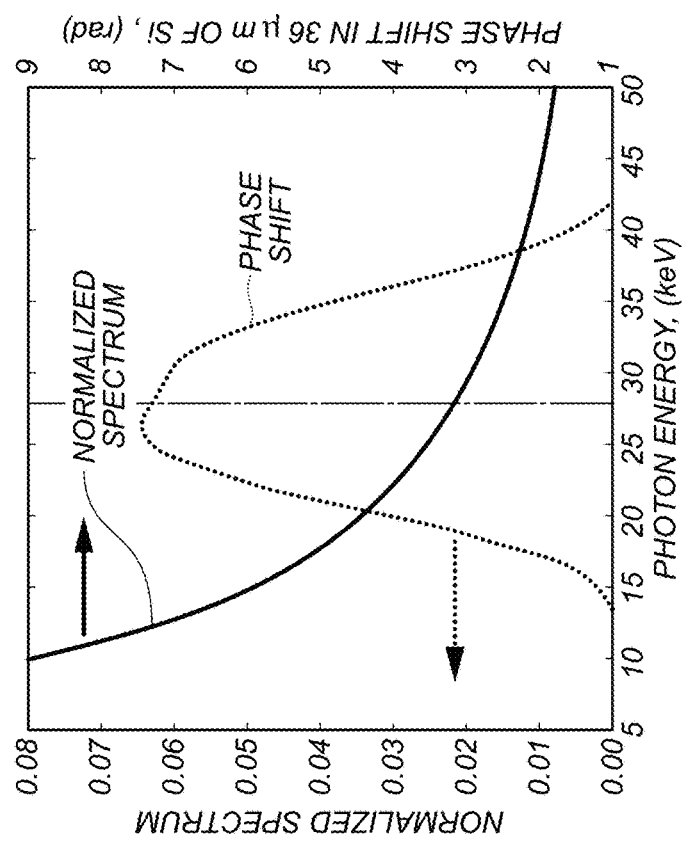

When the material of the phase grating and the operational energy of the X-ray beam are chosen, size h of the grating bars is fixed. In one embodiment, if Si material is used in the PCI setup with 28 keV designed energy, for example, the height of the bars should be h=36 Åm, based on an index of refraction for silicon of $6.1 \times 10^{-7}$, and a wavelength of 0.443 Å for the 28 keV energy level. The refraction index decrement is $n=1-\delta+i\beta$ where the imaginary part β contributes to the attenuation of the amplitude and the real part δ (refraction index decrement) represents the phase shift. If the X-ray energy is different from the designed value (i.e., 28 keV), the phase shift through the Si grooves is no longer optimal. This results in loss of phase amplitude and therefore system contrast. FIG. 9A shows the phase shift superimposed over the normalized X-ray spectrum plotted as a function of photon energy. As observed, the phase shift changes from $3\pi$ to about $\pi/2$ over the range of the 40 kVp tungsten X-ray spectrum. The phase amplitude that corresponds to such phase shift is plotted in FIG. 9B. Although the points with $3\pi$ and π phase shifts produce maximum contrast, the optimal setting would correspond to a π phase shift, where the fluence of the X-ray beam is high and the phase amplitude is at maximum (i.e., 28 keV). As seen in the plot, any energy deviation from the optimal value would reduce: 1) phase amplitude, and 2) photon fluence, which in turn, would result in loss of contrast.

As described herein, the performance of a PCI system is sensitive to the relative rotational alignment of $G_1$ and $G_2$ gratings. The $\theta=0.1°$ relative tilt of the gratings results in a Moiré fringe pattern rotated by about 45° and approximately a 20% drop in system contrast. The contrast drop of about 50% is expected at $\theta=0.2°$. The dependence of the Moiré fringe frequency on the tilt angle is consistent between the simulation and the experiment. The Moiré frequency is independent of the energy of the X-ray spectrum, which was shown analytically and experimentally. The L-d regions of best contrast were identified. Such regions showed a linear slope, which was consistent with the theoretical prediction.

As described herein, the relationships between an imaging system's contrast and its geometry may be used to optimize its assembly and setup. As shown herein, relative misalignment of the $G_1$ and $G_2$ gratings, relative to source grating $G_0$, does not dominate the contrast of PCI system because the distance between $G_0$ and $G_1$ (L) is significantly larger than the distance between $G_1$ and $G_2$ (d). However, the contrast does exhibit more sensitivity to alignment between $G_1$ and $G_2$. As disclosed herein, the imaging system may suffer about a 20% contrast drop for a $\theta=0.1°$ misalignment angle, which may further drop down to 50% when the misalignment angle is doubled ($\theta=0.2°$). Such behavior of the contrast was explained by the response of the X-ray detector to changes in the frequency of the modulated Moiré pattern caused by the relative rotations of the $G_1$ and $G_2$ gratings. It is disclosed herein that the angular sensitivity can be reduced if a detector with better frequency response was utilized (e.g., if a CsI scintillator is used rather than a $Gd_2O_2S$ or CMOS detector). The system contrast was analyzed as a function of distances L and d and found that the contrast can reach its maximum value at the specific range of L and d distances as shown in FIGS. 2A-D. Such an L-d range is relatively broad, which allows for an simpler retune of the system for a different L or d distance. The contour plots of FIGS. 2A-D suggested: i) linear L-d dependence and ii) constant frequency in the optimal L-d region. This behavior was predicted analytically by Eq. (10), which also indicated that the L-d region of optimal contrast does not depend on photon energy. The energy independence was confirmed in contrast scans conducted at different kVp settings (FIGS. 2A-D). As shown in FIGS. 9A-B, the phase grating structure (namely, the height of the grating's bars) is optimized for a specific X-ray spectrum (i.e., particular mean energy) and any deviation of spectrum from its optimum would reduce the contrast.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A method comprising:
    fabricating a phase grating and an absorption grating according to a preselected pitch;
    measuring an actual pitch of the fabricated phase grating and absorption grating; and
    fabricating a source grating based on the actual pitch of the fabricated phase grating and absorption grating.

2. The method of claim 1, further comprising disposing the fabricated source grating, phase grating and absorption grating in a phase contrast imaging system, wherein the phase grating and absorption grating are each disposed in one of a pair of parallel planes.

3. The method of claim 2, further comprising tilting one of the fabricated phase grating and absorption grating with respect to the other at a preselected tilt angle.

4. The method of claim 3, further comprising maintaining the phase grating and absorption grating in each of the parallel planes after the step of tilting.

5. The method of claim 2, further comprising placing an object to be imaged in the phase contrast imaging system and capturing a radiographic image of the object.

6. The method of claim 3, further comprising placing an object to be imaged in the phase contrast imaging system and capturing a radiographic image of the object.

7. The method of claim 2, wherein the step of fabricating the source grating includes selecting a dimension of the source grating according to $p_{int}=p_1(p_0+p_2)/(2p_0)$, wherein $p_0$, $p_1$, and $p_2$ are the selected dimensions of the source, phase, and absorption grating, and wherein $p_{int}$ is the period of the Moire pattern.

8. A method of assembling a phase contrast imaging system, the method comprising:
    fabricating a phase grating and an absorption grating according to a preselected pitch;

measuring an actual pitch of the fabricated phase grating and absorption grating; and selecting a source grating based on the actual pitch of the fabricated phase grating and absorption grating, wherein the step of selecting comprising moving one of a plurality of source gratings secured in a gratings holder of the imaging system into a path of an x-ray beam.

9. The method of claim 8, further comprising disposing the selected source grating, the fabricated phase grating and absorption grating in a phase contrast imaging system, wherein the phase grating and absorption grating are each disposed in one of a pair of parallel planes.

10. The method of claim 9, further comprising tilting one of the fabricated phase grating and absorption grating with respect to the other at a preselected tilt angle.

11. The method of claim 10, further comprising maintaining the phase grating and absorption grating in each of the parallel planes after the step of tilting.

12. The method of claim 9, further comprising placing an object to be imaged in the phase contrast imaging system and capturing a radiographic image of the object.

13. The method of claim 10, further comprising placing an object to be imaged in the phase contrast imaging system and capturing a radiographic image of the object.

14. The method of claim 8, wherein the step of selecting the source grating includes selecting a source grating from the plurality of source gratings that either:

satisfies $p_0/L=p_2/d$, wherein $p_0$ is the selected dimension of the source grating, L is a distance between the source grating and the phase grating in the phase contrast imaging system, $p_2$ is the period of the absorption grating, and wherein d is a distance between the phase grating and the absorption grating in the phase contrast imaging system, or provides a minimum difference between $p_0/L$ and $p_2/d$ from among the plurality of source gratings.

15. The method of claim 8, wherein the step of selecting the source grating includes selecting a source grating from the plurality of source gratings that satisfies $p_0/L - p_2/d=x$ wherein $p_0$ is the selected dimension of the source grating, L is a distance between the source grating and the phase grating in the phase contrast imaging system, $p_2$ is the period of the absorption grating, d is a distance between the phase grating and the absorption grating in the phase contrast imaging system, and wherein x is a preselected design value.

* * * * *